(12) United States Patent
Garms et al.

(10) Patent No.: US 6,439,040 B1
(45) Date of Patent: Aug. 27, 2002

(54) DEVICE FOR ANALYZING EXHAUST EMISSIONS FROM MOTOR VEHICLES

(75) Inventors: Stefan Garms; Michael Palocz-Andresen; Stefan Schroll, all of Hamburg (DE)

(73) Assignee: Wissenschaftliche Wekstatt fur Umweltmesstechnik GmbH (DE)

( * ) Notice: Subject to any disclaimer, the term of this patent is extended or adjusted under 35 U.S.C. 154(b) by 0 days.

(21) Appl. No.: 09/486,579

(22) PCT Filed: Aug. 24, 1998

(86) PCT No.: PCT/DE98/02494

§ 371 (c)(1),
(2), (4) Date: Feb. 25, 2000

(87) PCT Pub. No.: WO99/10728

PCT Pub. Date: Mar. 4, 1999

(30) Foreign Application Priority Data

Aug. 25, 1997 (DE) .......................... 197 36 864
Sep. 11, 1997 (DE) .......................... 197 39 869
Oct. 4, 1997 (DE) .......................... 197 43 954

(51) Int. Cl.$^7$ ............................................ G01N 21/00
(52) U.S. Cl. ................................ 73/118.1; 73/23.32
(58) Field of Search ........................ 73/23.31, 23.32, 73/118.1, 118.2; 60/276, 277

(56) References Cited

U.S. PATENT DOCUMENTS

| | | | |
|---|---|---|---|
| 3,696,247 A | * 10/1972 | McIntosh et al. ............... 356/51 |
| 4,160,373 A | * 7/1979 | Fastaia et al. ............... 73/23.31 |
| 4,801,805 A | * 1/1989 | Butler et al. ................ 250/343 |
| 5,184,017 A | 2/1993 | Tury et al. | |
| 5,498,872 A | * 3/1996 | Stedman et al. ......... 250/338.5 |
| 5,591,975 A | * 1/1997 | Jack et al. ................ 250/338.5 |
| 5,621,166 A | * 4/1997 | Butler ........................... 73/116 |
| 5,709,082 A | * 1/1998 | Harris et al. .................... 60/276 |
| 5,793,043 A | 8/1998 | Weckstrom et al. | |
| 6,181,419 B1 | * 1/2001 | Snelling et al. ............. 356/335 |

FOREIGN PATENT DOCUMENTS

| | | |
|---|---|---|
| DE | 41 21 520 A | 1/1992 |
| DE | 196 05 053 A | 9/1996 |

* cited by examiner

*Primary Examiner*—George Dombroske
(74) *Attorney, Agent, or Firm*—Schnader Harrison Segal & Lewis LLP

(57) ABSTRACT

This description refers to a device for analyzing the most important environmentally relevant substances, such as CO, HC and NO, that are present in vehicle exhaust emissions. It is based on the principle of IR gas absorption. This involves producing measuring signals and a reference signal in a measured optical length (stainless steel tube), with the aid of an infrared source and detector. The production of a ratio then gives a reading and a warning signal is produced whenever a certain limit value is exceeded. The OBM system is made up of modular components, such as a sampling device, exhaust gas processing unit, analyzing device and evaluation unit, which are built into the vehicle. The fluctuating conditions present in the vehicle are compensated for by robust construction and correction of temperature drift by means of production of the first derivation and readjustment of signal strength using an electronically regulated amplification control. Further correction possibilities are: calibration of the zero line using ambient air via a switchover system, and the establishment of a tolerance limit around the noise signals in the detector. The measuring system should in future be installed in all motor vehicles as an extension to using OBD (on board diagnosis) systems. Modification kits are available for older vehicles.

15 Claims, 10 Drawing Sheets

DEVICE FOR ANALYZING EXHAUST EMISSIONS FROM MOTOR VEHICLES

The exhaust emissions of passenger and commercial vehicles are the cause of various types of harm to the environment. The introduction of emission-limiting legislation has forced, and is forcing, vehicle manufacturers to reduce the emissions of individual vehicles by—for example—developing advanced engines and exhaust systems.

One reason for a vehicle failing to conform to emission regulation is worsening performance, in terms of a gradual increase in exhaust emissions, as the vehicle ages. This is caused by wear and also, in part, by the incorrect functioning of components in the drive and emission-reduction systems.

The normal inspection procedure involves regular tests to attempt to keep emissions at or near their original level. The disadvantage of this method is that faults remain undetected until the next inspection, and excessive emissions meanwhile continue to be produced.

In the first few seconds after the engine is started, the catalytic converter—which has not yet reached its running temperature—barely affects the level of harmful exhaust emissions. An engine produces about 70% of its total emissions just after starting from cold, so an ideal system for reducing harmful emissions would cover this phase, which is precisely the phase that remains untouched by current systems of emission control detection.

THE STATE OF THE ART

"On board diagnosis" (OBD) is one new system for reducing harmful emissions. The term refers to an emission control system which uses sensors to monitor the performance of those individual components of a passenger or commercial vehicle that have a bearing on exhaust emissions. An early version of OBD for passenger cars—the OBD I Law—has already been in use for a considerable time in the USA and is gradually being superseded by the more stringent OBD II Law for models from 1995 onwards. While OBD I only affected the performance monitoring of components forming part of an electronic engine control system, OBD II requires the control of all components relevant to emissions. The law expressly stipulates the monitoring of catalytic converters, lambda probes, fuel systems, air injection systems, exhaust gas recirculation, tank ventilation and the detection of misfiring. In the event of a component breaking down or malfunctioning, a warning lamp lights up on the dashboard and an error code is memorised. The fault detected should be located as precisely as possible and described. The information is then stored in order to permit swift identification of the fault at the workshop (using a standard interface) and to allow repair of the defective part.

A further step in this field is the use of "On Board Measurement" (OBM). Systems for the direct analysis of vehicle emissions are widely familiar. Some examples, among many others, are the German public patents 32 32 416, 33 39 073, 36 08 122, 37 16 350, 39 32 838, 40 05 803, 41 24 116, 42 35 225, 43 07 190, the DE specification 43 19 282 C1 and U.S. Pat. No. 4,803,052 and 5,281,817, along with further patent applications GB 2 264 170 A, EP 0 196 993 A2 and WO 94/09266. These documents should be referred to for explanations in greater detail of items mentioned here.

Applications /1/ and /2/ are concerned, in a narrow sense, with subjects related to this field and are dealt with in greater detail for this reason. Thus patent /1/ describes an infrared measuring system that monitors the operating condition of the catalytic converter via a lateral access opening in the unit and measures the gases present inside. In /2/, the system in question is a rapid detector that uses several infrared cells connected in series to permit a chronological resolution of 0.1–0.2 sec. Neither source gives an indication of continuous measurement of harmful exhaust system emissions upstream of the catalytic converter.

Written sources reveal that no current measuring system is capable of providing a continuous record of actual emissions, either in the cold-start phase or during operation. Neither is it possible to detect fluctuations or indicate faults.

DESCRIPTION OF THE OBJECT OF THE PATENT

Vehicles will, in the future, be fitted with an integrated OBM system for the purposes of emission analysis. This system will analyse certain elements of the exhaust gases, and a comparison of current concentrations with a set of stored target values will permit the detection of faults in the ignition system. A warning system will then be activated whenever the "satisfactory" level specified for the individual model of vehicle is exceeded, clearly and repeatedly, over a period. "Over a period" means an extended length of time, "repeatedly" signifies an excessive reading on not one, but various occasions and "clearly" refers to a concentration that is outside the margin of tolerance specified.

FIG. 1 shows an example of how the concentration of harmful substances is affected by faults in the ignition system (caused by misfiring (1) in this case).

The measurement of emissions is hindered by the fluctuating conditions present in the vehicle. A measuring system must on one hand keep to the general margins of tolerance and specifications valid for the vehicle while, on the other hand, it is precisely the exhaust-related elements of pressure, moisture, temperature and flow rate that are subject to sharp fluctuations. In order to solve this problem, especially robust micro system components are required—both for exhaust gas processing and for the detection of the elements of which the gas consists.

One device for the analysis of vehicle exhaust gases is already familiar in the shape of DE 196 05 053 A1. Problems related to specified operation have however been encountered with this device, as they have with measuring devices described in other documents. The presence of vibrations in the vehicle requires that measuring systems be of highly stable construction and also resistant to soot, dust and aerosol precipitation. They must furthermore attain a high level of resolution, as the constituent components of the exhaust gas being analysed—e.g. carbon monoxide (CO), hydrocarbons (HC), and oxides of nitrogen (NO)—are present in extremely low concentrations, precisely in those petrol-driven vehicles that are fitted with a catalytic converter.

The emission analysis method used in the new OBM system submitted here is an infrared gas absorption process. This invention is based the assumption that, in order to obtain the required resolution, optical path length must be increased. The optical cell can thus be fitted to a vehicle if it is incorporated at the construction stage.

BRIEF DESCRIPTION

TECHNICAL DESIGN OF THE MEASURING SYSTEM

Figure 1:
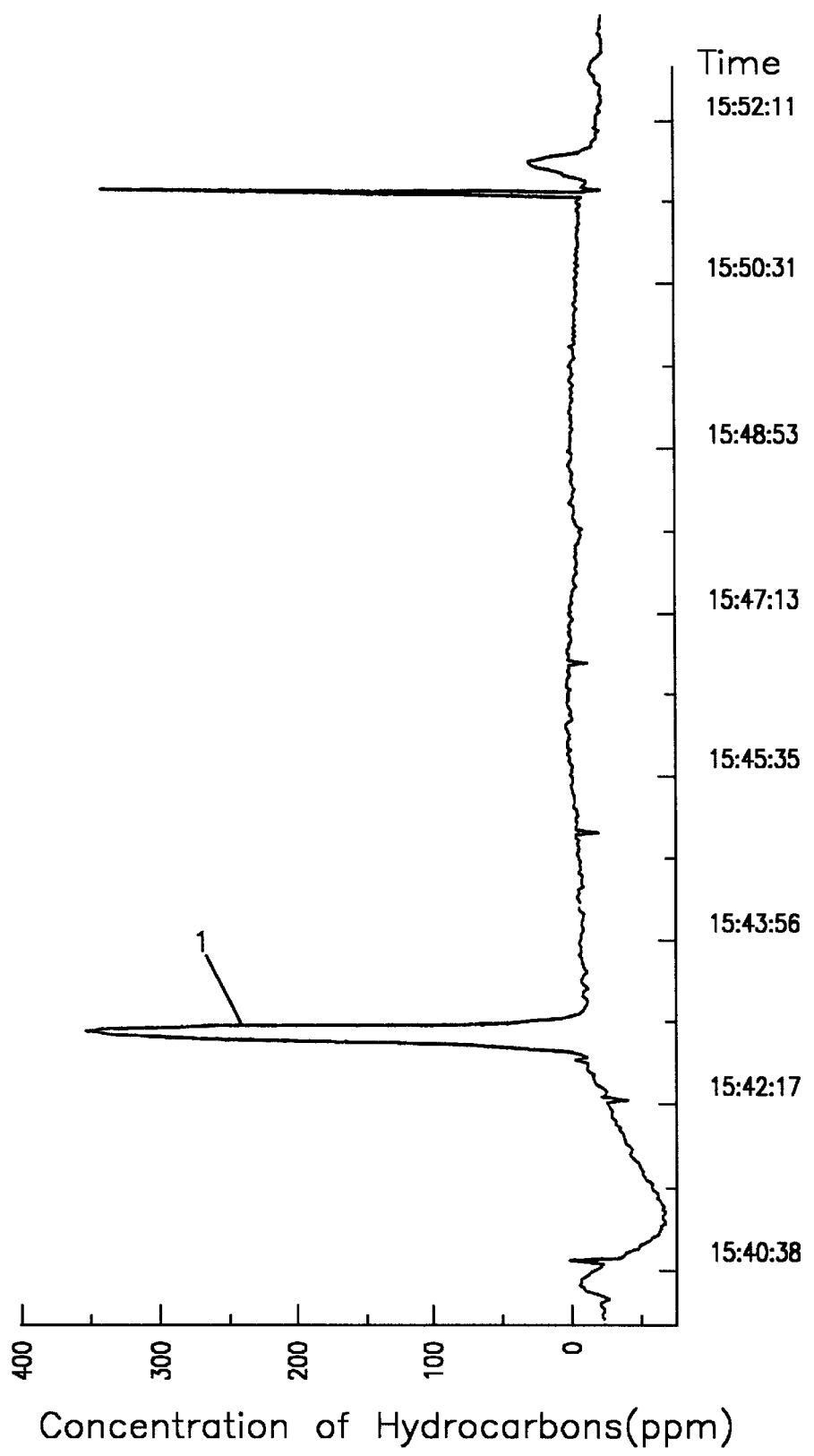
FIG. 1 is a graph representing contaminant concentrations caused by misfiring.
Figure 2:
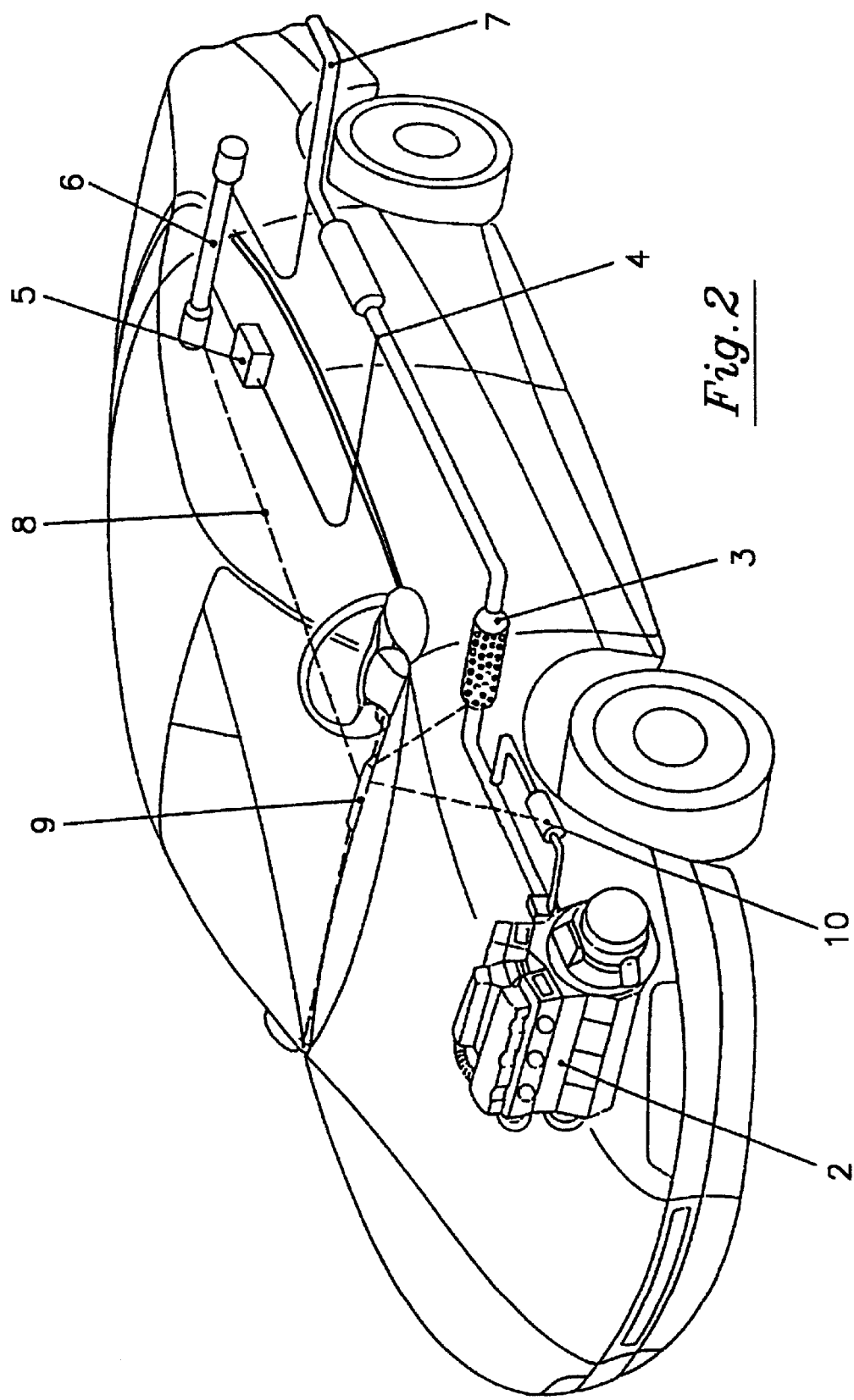
FIG. 2 is a perspective view of the main installation of the OBM system inside the motor vehicle.

The main assembly of the OBM system in a vehicle is shown in FIG. 2, along with the main components of the ignition system. The engine (2) produces exhaust fumes as it burns fuel. In the catalytic converter (3), harmful elements are transformed into less toxic substances. The vehicle OBM system consists of the sampling point (4), exhaust gas processing unit (5), analysing device (6), exhaust system (7) and data cable (8) that provides the link between the display unit (9) and analysing device (6).

Gas is extracted from the exhaust system upstream of the catalytic converter, as this is the only way in which an evaluation of the condition of the ignition system as a whole can be made.

Figure 3:
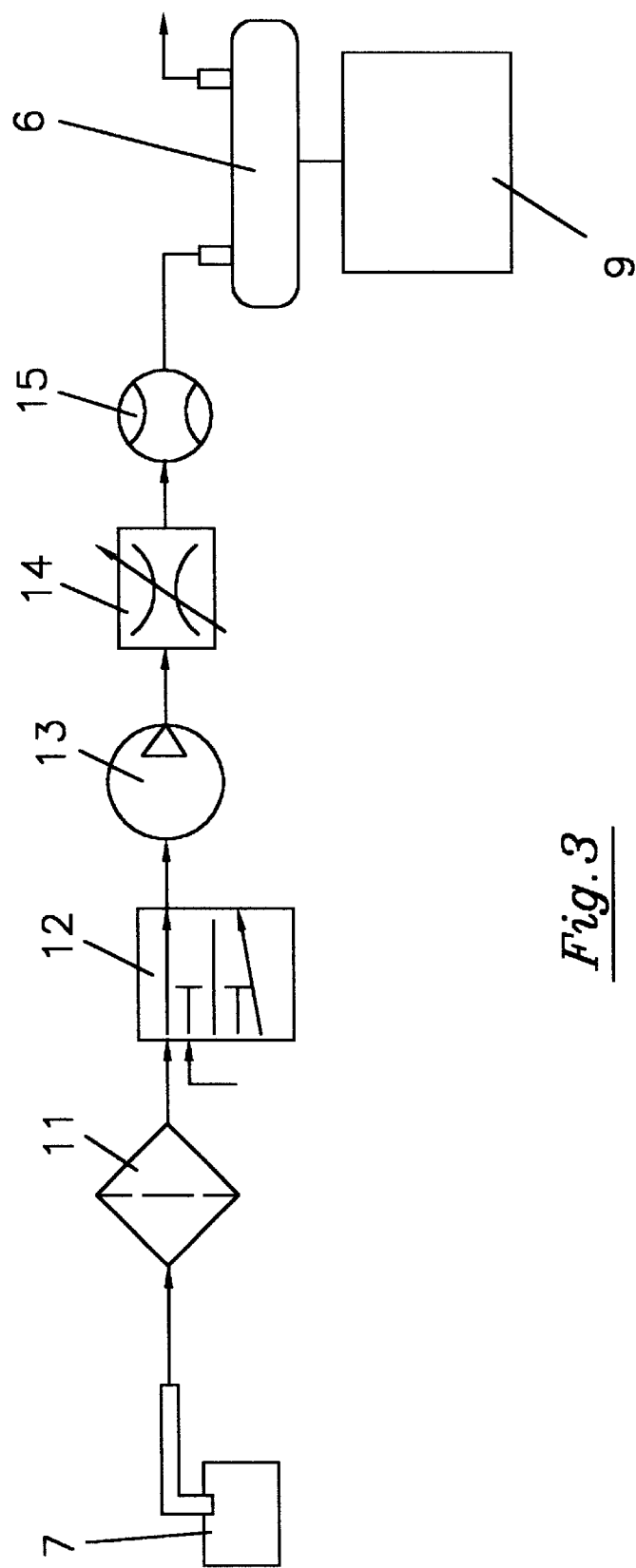
FIG. 3 is a block diagram of the exhaust processing unit gas flow diagram.

Exhaust gas processing is illustrated in the gas flow diagram (FIG. 3). Soot and particles are removed from the exhaust gas using a disposable filter (11). A solenoid valve (12) is used to change over between exhaust gas and calibration gas (see chapter 7). The measuring gas pump (13) sends the gas to be measured to the analysing device (6) via the pressure reducer (14) and flow meter (15).

Exhaust gas analysis is carried out in the analysis device (optical cell) following the principle of infrared gas absorption. This device consists of an infrared source (transparent tube), the radiation from which is directed to the measuring head via a measured length (optical cell). The optical cell can consist of one straight, highly reflective tube or of several tubes with reflective heads. The two pyroelectric measuring sensors fitted to the measuring head are equipped with various optical filters and produce one signal that depends on measurements and another which acts as a reference signal. The ratio formation of these signals reduces the disturbing influences (temperature, pressure, contamination) acting on the measuring signal. The use of the pyroelectric principle requires a synchronised radiation source. Electrical timing of the radiation source avoids delicate mechanical components (chopper). The measuring system is thus rendered more robust, with an optical cell (measured length) made of stainless steel. In the event of the device being contaminated or suffering component faults, the advantage of the modular construction of the unit becomes clear. Single components such as filters can simply be replaced.

Modification Kit for Emission Analysis on Older Vehicles

In the case of older vehicles, which have not been fitted by the manufacturer with an OBD or OBM system, engine and exhaust gas processing performance cannot be measured other than by analysis of the exhaust gas itself. For this reason, a modification option should be available.

The disadvantage of carrying out modifications with an OBD system is the large number of transducers, for which there is neither sufficient room nor electronic connections. It is therefore more convenient to install an on board measuring system.

Figure 4:
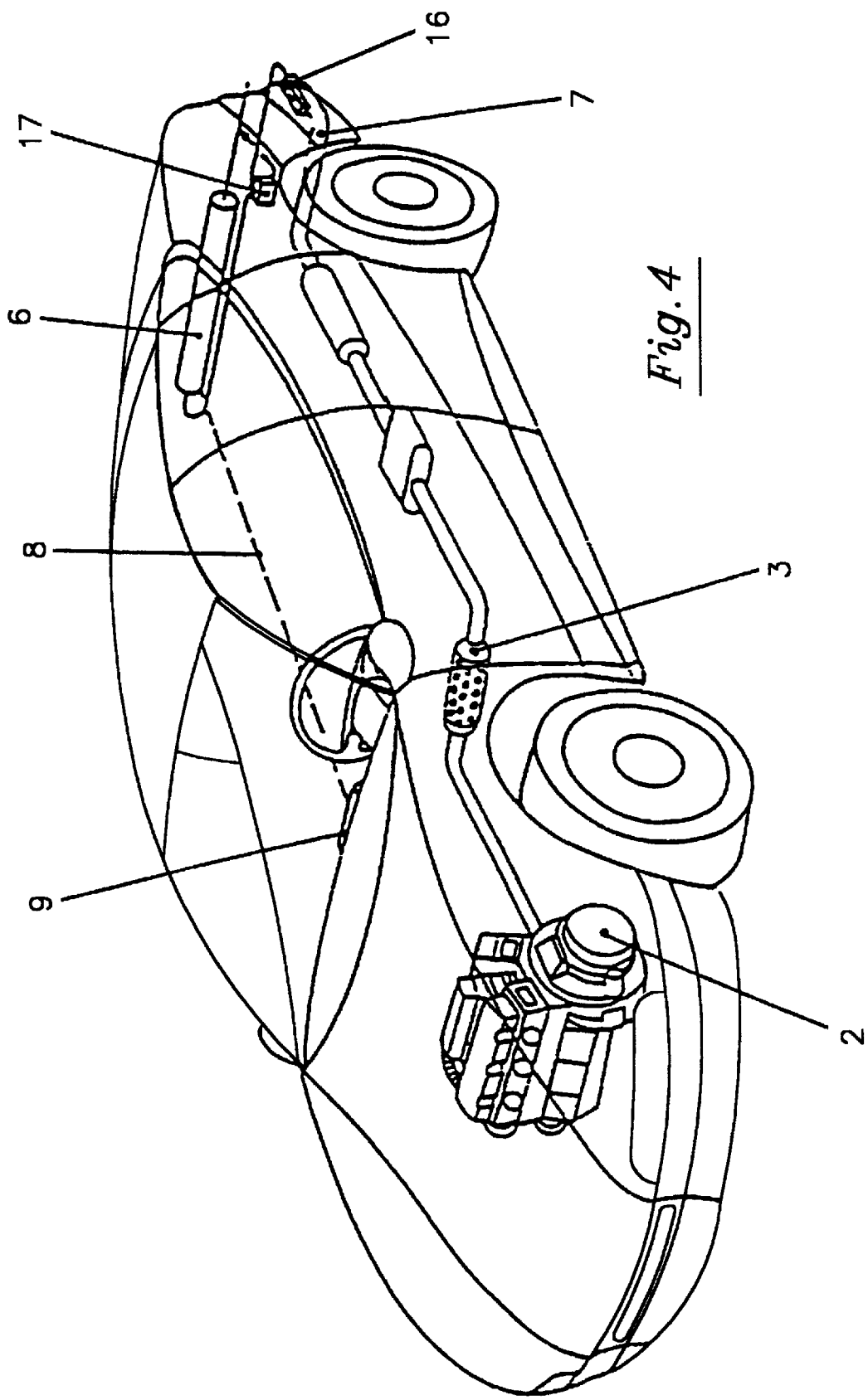
FIG. 4 is a perspective view of the main layout of modification kit.

FIG. 4 shows a modular OBM modification system of this type. Exhaust gas sampling is carried out using a sampling sensor (16) fitted to the end of the exhaust pipe. The gas is cleaned and dried in the exhaust gas processing unit (17) and then pumped onwards to the analysing device (6). The display unit (9) on the dashboard then indicates information about the status and operation of the OBM system.

Figure 5:
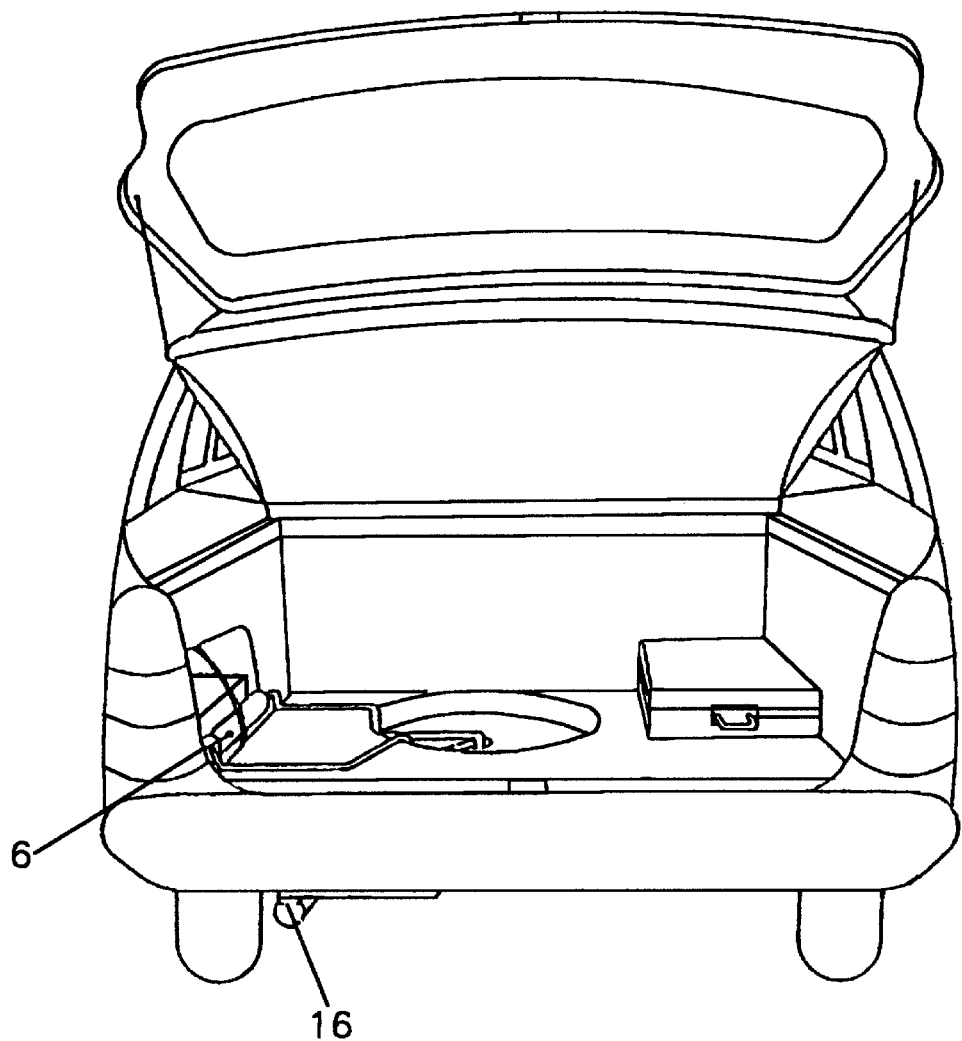
FIG. 5 is a rear view of the fitting of the modification kit in the car boot.

The fitting of the modification kit to the vehicle is illustrated in FIG. 5. This involves attaching the sampling sensor (16) to the end of the exhaust pipe, while the analysing device (6) and gas processing unit (17) can be installed in the car boot. The display unit (9) can be hung from a ventilator grille or fitted elsewhere on the dashboard.

Cold-start Measurement and Adsorption Trap

Figure 6:
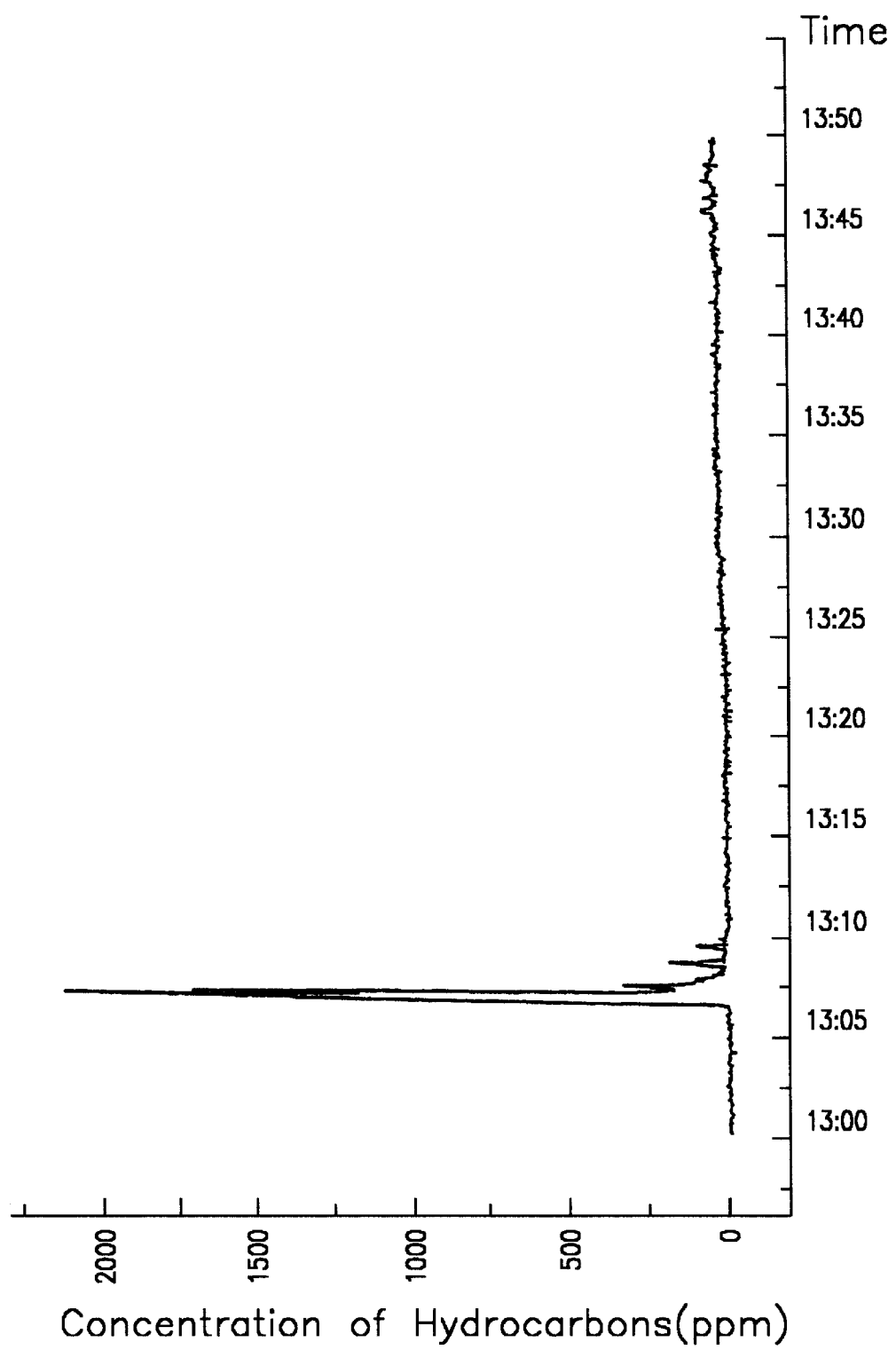
FIG. 6 is a graph representing cold-start measurement.

The cold-start phase (see FIG. 6) is when 70% of total engine emissions are produced, and an on board measurement system calibrates these gases. These readings can be used to activate an HC adsorption trap (10, see FIG. 2) used for collecting cold-start emissions in the exhaust flow path. Emission measuring makes it possible to synchronise the adsorption trap in the exhaust flow path to activate at exactly the right moment, or to start desorption. Desorption of the small amount of retained hydrocarbons until the catalytic converter reaches a temperature at which satisfactory conversion is guaranteed.

The energy consumption of the cold-start measuring system is extremely low, so it can enter operation before the cold-start phase has actually commenced. Control can be carried out, for example, by means of either a seat occupation sensor or a sensor on the ignition lock, which can also be used to activate the HC adsorption trap in the exhaust flow path.

Reference Line Calibration

The measuring principle of infrared gas absorption is sufficiently well known. The problems with this measuring principle with regard to fluctuating ambient conditions have already been described in section 3. We will now examine the various measurement correction methods used.

Figure 7:
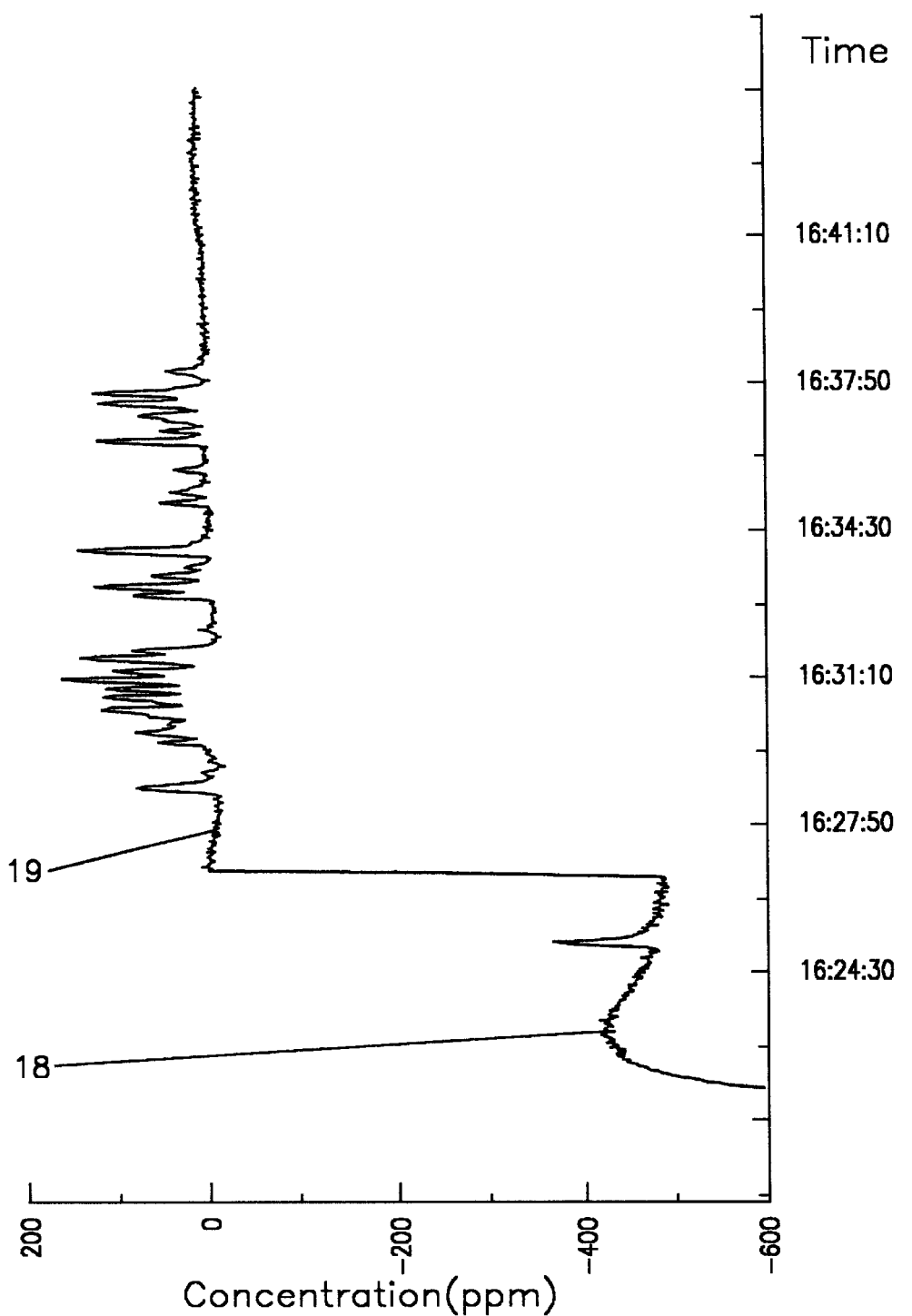
FIG. 7 is a graph representing a zero-line correction.

The most common problem is the shifting of the zero point—i.e. the reading for uncontaminated gas is not zero. This problem can be solved by calibrating the system with ambient air, proceeding as follows:

The solenoid valve (12) in the exhaust gas processing unit (5,17) is automatically switched over either after a pre-set period or as a result of detected external factors, allowing ambient air to enter the analysis device (6). The concentrations of CO, HC and NO present in the ambient air are so low that they can safely be regarded as zero. The use of mathematical compensation allows the zero line to be calibrated. After this has been carried out, the sensitivity of the device usually recovers its original levels and the system begins once again to display reproducible readings. FIG. 7 shows the effect of a zero line correction. The graph illustrates how the zero line (18) has been displaced by temperature drift and also shows the re-corrected measuring curve (19) produced after calibration. This procedure, with an interruption in emission recording, has no influence in terms of nominal values on the meaningfulness of measurements, whose purpose is—in any case—the detection of faults in the exhaust system rather than the providing of continuous monitoring.

Adjusting the Sensitivity of the Measuring Signals Using the $CO_2$ Concentration of the Ambient Air The zero-calibration procedure described in section 7 has the advantage of avoiding the need for constant sensitivity adjustment, as this procedure also produces the right correction for the sensitivity level (and thus all others). A sensitivity check can nevertheless be carried out as follows:

The atmosphere in all parts of the world (with clean non-city air) has an average $CO_2$ concentration of 350 ppm. This fact can be used to check sensitivity, as this concentration matches the measuring ranges of the components normally detected in the stream of exhaust gas. CO, HC and—above all—NO in fact have weaker absorption bands than $CO_2$, but with correspondingly higher peak concentrations. According to the Lambert-Beerschen equation, the same optical cell length or—in practical terms—the same optical cell, can thus be used. If uncontaminated ambient air is now fed into the exhaust gas analysing device (6), the system should show the average $CO_2$ concentration—once the zero point reset procedure described above has been carried out. One can now be sufficiently sure that the sensitivity level of the other measurement factors is also correct.

Figure 8:
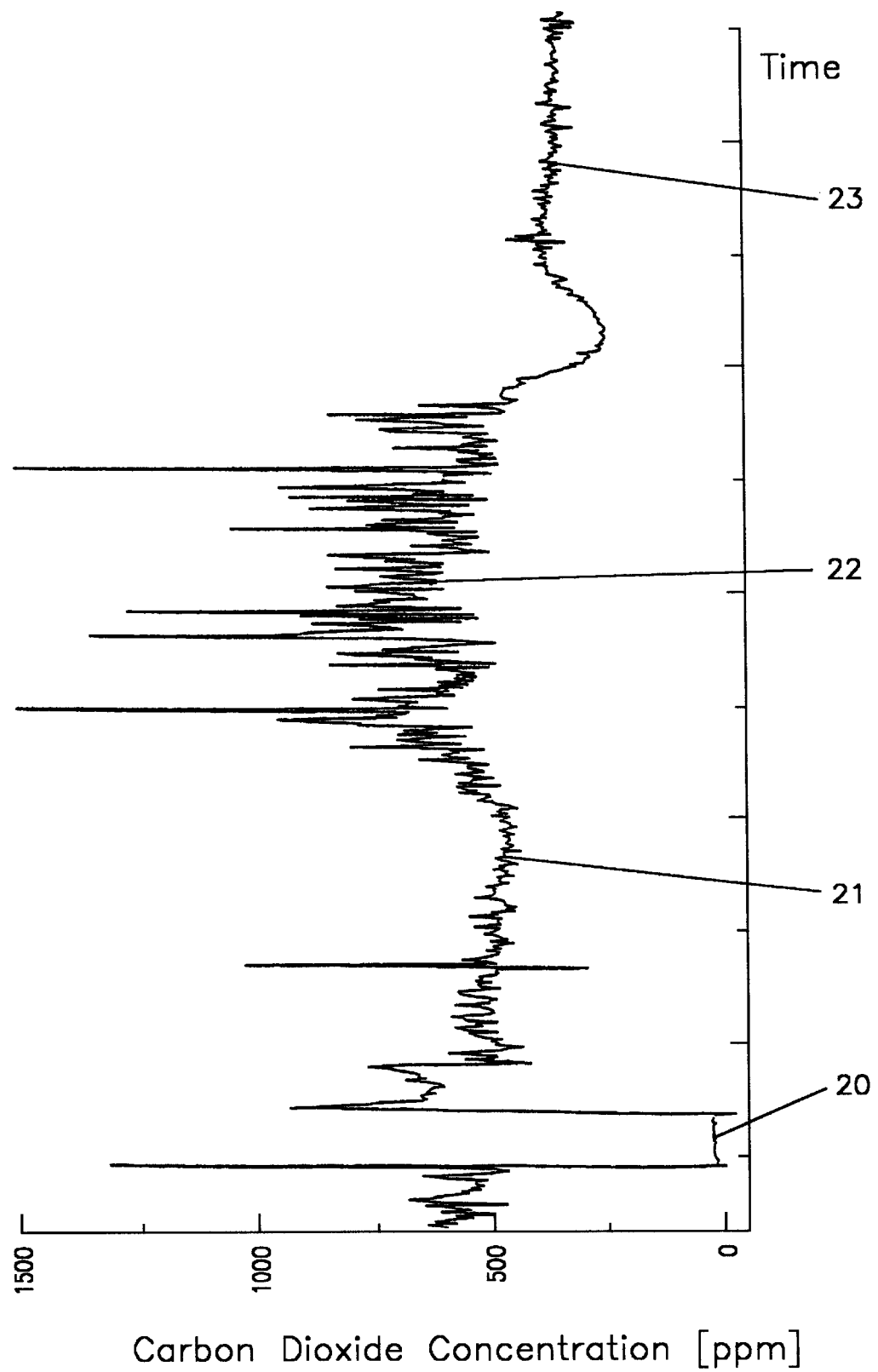
FIG. 8 is a graph representing carbon dioxide concentration in ambient air.

The disadvantage of the above procedure is that local $CO_2$ concentrations fluctuate sharply due to external influences. This is especially true in densely populated areas, where road traffic can produce extremely high concentrations of $CO_2$. FIG. 8 shows the carbon dioxide concentration of the ambient air during a test drive. After adjustment of the zero point using synthetic air (20), the vehicle was driven through a small municipality (21) where the $CO_2$ concentration was relatively constant. A test drive through a larger town (22) with crossings and traffic lights reveals high, sharply-fluctuating $CO_2$ concentrations. Finally, a measurement carried out in a quiet interior courtyard (23) is closer to a natural $CO_2$ concentration.

Sensitivity Adjustment Via the $CO_2$ Concentration in the Exhaust Gas

One possible way of avoiding the problems resulting from the fluctuations from natural $CO_2$ concentrations described in section 8 is the monitoring of the $CO_2$ concentration in the vehicle exhaust The ignition process makes this value relatively stable, so that this concentration can be used as a reference value for adjusting the sensitivity of the individual meter flumes. However, the high concentration (12% by volume) of $CO_2$ in the exhaust gas means that the $CO_2$ beam path in the optical measuring cell must be arranged differently to that used for other harmful gases. The optical path for $CO_2$ measurement basically has to be shorter than that used for the contaminants CO, NO and HC.

Correction—using a Software-controlled Filter—of Zero Line of Measuring Signal Displaced Due to Temperature Fluctuations A measurement value is normally determined by the production of a ratio from the signal for the contaminant present (measuring signal) and the reference signal.

The signal progressions for measuring signals and reference signals reveal a great similarity. A ratio procedure can thus be modified if a certain margin of tolerance is determined around the signal progression and the ratio is set to "one" within this margin. This allows a range for zero concentration to be obtained, and only in the event of this margin of tolerance being exceeded will a concentration corresponding to the values of the then determined real ratio be displayed. Note: the concentration "zero" need not necessarily correspond to the ratio "one", but it does obtain the best measuring result.

Figure 9:
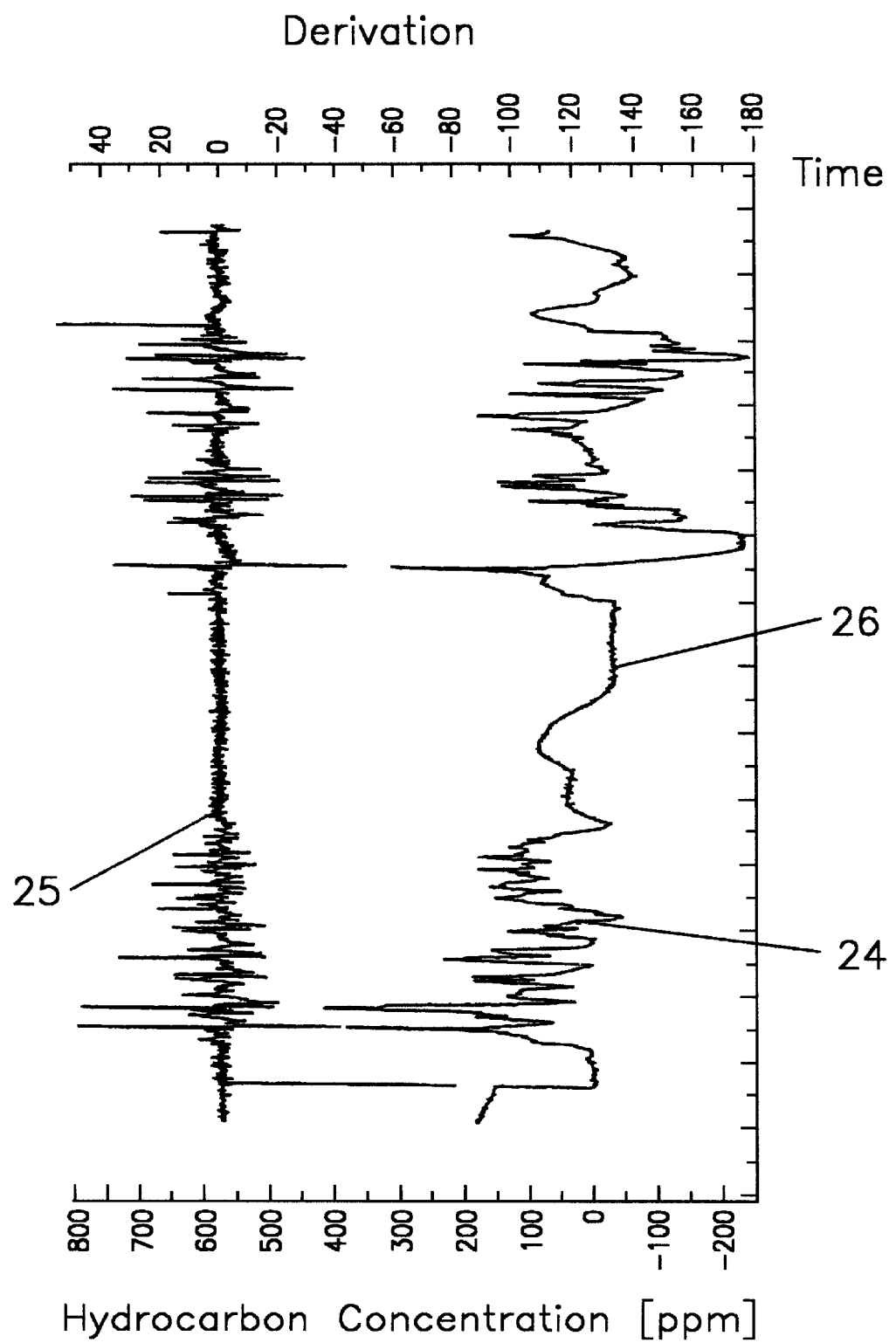
FIG. 9 is a graph representing the derivation in correction function.

Compensation of Temperature Drift by Examination of the Dynamics of the Signal Progressions Experience shows that extreme dynamic conditions are present in motor vehicles (brusque momentary system alterations, compared to the cycle period of the radiation emitter). This means that it is easy to differentiate between genuine measuring signals (i.e. those produced by the exhaust gas) and the slower—fluctuating variations that depend on temperature. To carry out correction, the first derivation of the concentration process must be produced according to time. The first derivation records only genuine step functions that occur, for example, when the vehicle accelerates. FIG. 9 shows an actual measuring value progression. The first derivation (25) was produced from the original measuring signal of contaminant HC (24). It can be clearly seen that measurement signal fluctuations (26) provoked by the influence of temperature approach zero in the derivation (25).

Once the step function places from the first derivation have been found according to time, the points can be recognised with clear step characteristics. If such a genuine step function appears, i.e. if a measurement value exceeds the previously defined margin of tolerance by a permitted amount relative to the differential curve, this point must be used as a reference relative to the actual concentration curve used for evaluation. When the first derivation returns to zero, the software-controlled filter once again emits the zero line as an unaltered, stable line. Thus you have at your disposal during the test drive one of two things. The first possibility is an absolute zero line—without fluctuations, as no step functions have appeared and the fluctuations caused by temperature are ignored. The other possibility is that whenever real, dynamic step functions occur, such as when accelerating, changing gear, braking, etc., the original measuring signals (obtained from the concentration curve) are observed according to the first derivative.

Setting the Original Signal Strengths in the Channels of the IR Gas Analyser

A further correction method involves resetting the signal strength by means of an electronically regulated amplification controller.

Since the margin of reference for infrared gas absorption is set in such a way that virtually no absorption takes place at this limit, the infrared detector reference channel measuring signal should always maintain its original strength. The effects of temperature and vehicle wear do however cause noticeable fluctuations in this signal.

Figure 10:
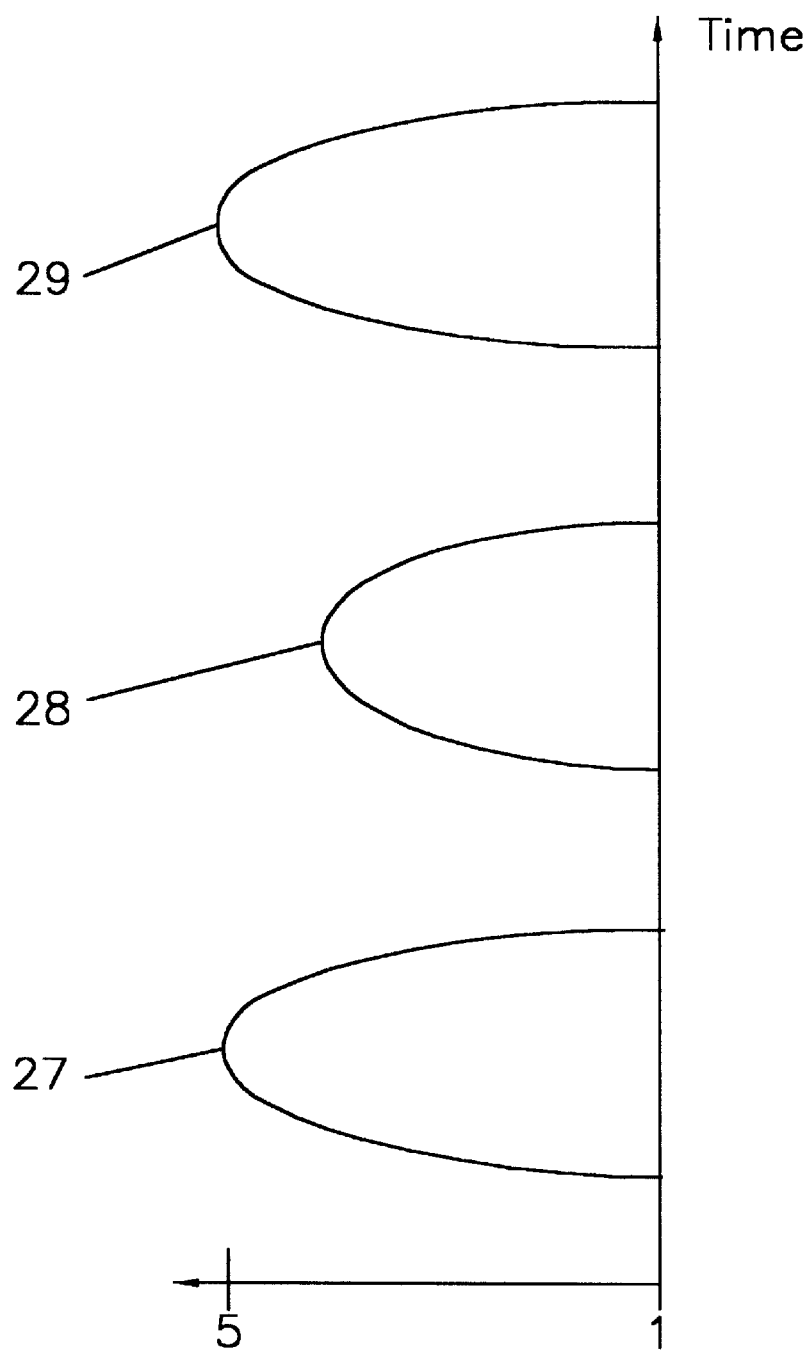
FIG. 10 is a graph representing correcting signal strength.

In order to compensate for the signal fluctuations caused by temperature conditions, the possibility exists to monitor continuously the reference signal by means of a measurement, control and regulating device built into the system. Whenever the reference signal deviates by a predefined margin from the value originally adjusted at initial calibration, all signals are realigned—using an electronically regulated amplification controller—with the original signal strength. FIG. 10 shows the original curve for the reference signal (27), the weakened curve resulting from wear or temperature drift (28) and the curve that has been corrected by electronically controlled amplification (29). This method retains the full range of signal dynamics.

What is claimed is:

1. A device to analyze environmentally relevant substances comprising at least one carbon monoxide (CO), hydrocarbons (HC), and nitrogen monoxide (NO) sensor located in a working section, separated from the exhaust gas system, wherein a pump system alternately delivers exhaust gas from the exhaust gas system and clean ambient air from the atmosphere through the working section.

2. The device according to claim 1, wherein the sensor works with the infrared gas absorption.

3. The device according to claim 2, wherein the working section consists of steel and has an optical distance of a minimum of 50 cm.

4. The device according to any one of claims 2 or 3, wherein the sensor has a halogen micro radiator that is surrounded with a transparent piston.

5. The device according to any one of claims 2 or 3, wherein the sensor receives light of a radiation source with a meter flume/reference channel at the same time and makes a quotient from the signals to explore the measurement values.

6. A device to analyze environmentally relevant substances such as carbon monoxide (CO), hydrocarbons (HC), and nitrogen monoxide (NO) in exhaust gas, with at least one sensor located in a working section, separated from the exhaust gas system, wherein a pump system alternately delivers exhaust gas from the exhaust gas system and clean ambient air from the atmosphere through the working section, wherein the pump system comprises an exhaust gas filter, adapted to be regenerated by heating, a solenoid valve and a measuring gas pump.

7. The device according to claim 6, further comprising a reducing regulator, and a flow meter.

8. A device to analyze environmentally relevant substances such as carbon monoxide (CO), hydrocarbons (HC), and nitrogen monoxide (NO) in exhaust gas, with at least one sensor located in a working section, separated from the exhaust gas system, wherein a pump system alternately delivers exhaust gas from the exhaust gas system and clean ambient air from the atmosphere through the working section, wherein divergent signal courses of two infrared sensitive detector cells (reference—and flow-measuring flume), caused by drifts in temperature, are superposed in measuring periods between zero phases.

9. The device according to claim 8, wherein signal height is adjusted in relation to a reference signal by an electronic adjustable gain control.

10. The device according to claim 9, wherein signal course drifts caused by temperature will be adjusted according to rapid concentration changes in normal vehicle usage by taking a first differential derivation of a concentrated course.

11. The device according to claim 10, wherein adjustment of the delicacy is performed by consideration of natural $CO_2$-concentration in clean ambient air (340 ppm normal value) or by consideration of a $CO_2$-part in the exhaust gas (14 Vol. %).

12. The device according to claim 11, wherein the device is placed at an underbody of the vehicle, in a luggage boot, in body of the vehicle or at other suitable places of the vehicle.

13. The device according to claim 12, wherein the device is integrated in the construction of the vehicle comprising a heated tapping place, exhaust gas preparation, analysis device, data line and display unit, whereby the single components are exchangeable by the modular construction and may be installable later.

14. The device according to claim 13, wherein the device is switched on with a seat loading sensor or an ignition lock sensor that measures a cold start from the beginning.

15. The device according to 14, wherein the measuring signal controls combustion procedures in an engine connected to the system and is a catalyst to recognize defects.

* * * * *